United States Patent [19]

Douglas, Sr.

[11] Patent Number: 4,909,804
[45] Date of Patent: Mar. 20, 1990

[54] CHILD'S TOILET TRAINING PANTS

[76] Inventor: Herman Douglas, Sr., Box 174, Norristown, Pa. 19404

[21] Appl. No.: 202,510

[22] Filed: May 3, 1988

Related U.S. Application Data

[63] Continuation of Ser. No. 861,864, Apr. 28, 1986, abandoned.

[51] Int. Cl.[4] .............................................. A61F 13/16
[52] U.S. Cl. ................................. 604/385.2; 604/396
[58] Field of Search .................. 604/385.1, 385.2, 394, 604/396, 366

[56] References Cited

U.S. PATENT DOCUMENTS

| | | | |
|---|---|---|---|
| 2,834,347 | 5/1958 | Connally | 604/385.1 |
| 4,205,679 | 6/1980 | Repke | 604/366 |
| 4,527,990 | 7/1985 | Sigl | 604/385.2 |
| 4,619,649 | 10/1986 | Roberts | 604/396 |

Primary Examiner—C. Fred Rosenbaum
Assistant Examiner—Mark O. Polutta

[57] ABSTRACT

A child's toilet training pants has an outer plastic waterproof sheet, a coextensive in size inner sheet of soft material to go next to the skin, an intermediate strip as wide as the space between the leg openings of highly water absorbent material, stitches at both sides above the leg openings and elastic bands at the waist and leg openings, said elastic bands not being caught up in the side stitches so that the stitched seams can readily be pulled apart to open up the pants.

4 Claims, 1 Drawing Sheet

CHILD'S TOILET TRAINING PANTS

This application is a continuation of application Ser. No. 861,864 filed Apr. 28, 1986, abandoned.

This invention relates to children's training pants and particularly ones which are principally intended to be disposable and to be quickly removable from the child.

Training pants of this type are disclosed and claimed in my copending patent application Ser. No. 168,264 filed on July 10, 1980 Abd and the feature of those pants is that they can easily be torn open at the side seams so they can readily be removed from the child when they are soiled. Ordinary training pants have to be pulled down off of the legs and this creates the risk of dirtying the child's legs. The training pants of my prior application eliminates the possibility of such contamination of the child's legs.

The present invention provides an improvement upon the pants of my earlier application. The present training pants absorb liquid better, they are easier to make and they have a more attractive appearance. These and other benefits are obtained and the former advantage of being easily torn open for removal is achievable.

A preferred embodiment of the invention is illustrated in the drawings in which.

Referring first to the blank form of FIGS. 1 to 4, it is made up of three pieces. The first sheet 11 is a thin plastic, waterproof material such as vinyl which will not transmit moisture and which will constitute the outer facing of the training pants. The inner facing of the pants is the thin sheet of moisture absorbent material 13 and it preferably is a non-woven film of cellulosic fibers. The central, in-between strip 12 is of highly absorbent material such as cotton batting.

Figure 5:
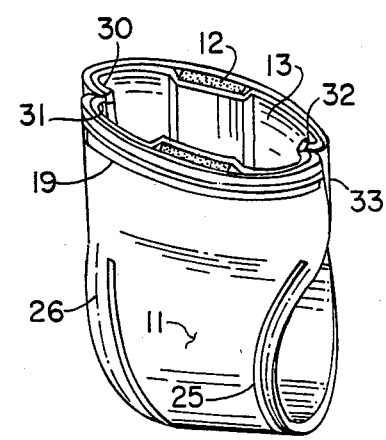
FIG. 5 is a perspective of the finished pants made from the blank of the above figures.

The sheets 11 and 13 are oblong and in their long sides are cut the circular notches 14 and 15 to form the leg openings of the finished pants as is clear from FIG. 5. These sheets 11 and 13 are coextensive in size and may be cut with the same pattern and they are of a size to fit the intended child of a designated age, when folded as in FIG. 5. Ordinarily, the blanks of FIGS. 1 and 2 will be more or less twice as long as wide.

The strip 12 of highly moisture absorbent material is as long as the outer sheets but is only as wide as the space between the notches 15 and 14 at the narrowest place. Of course, this strip 12 could widen out on both sides of this narrowest point if it is desired to have more moisture absorbent material present.

Figure 1:
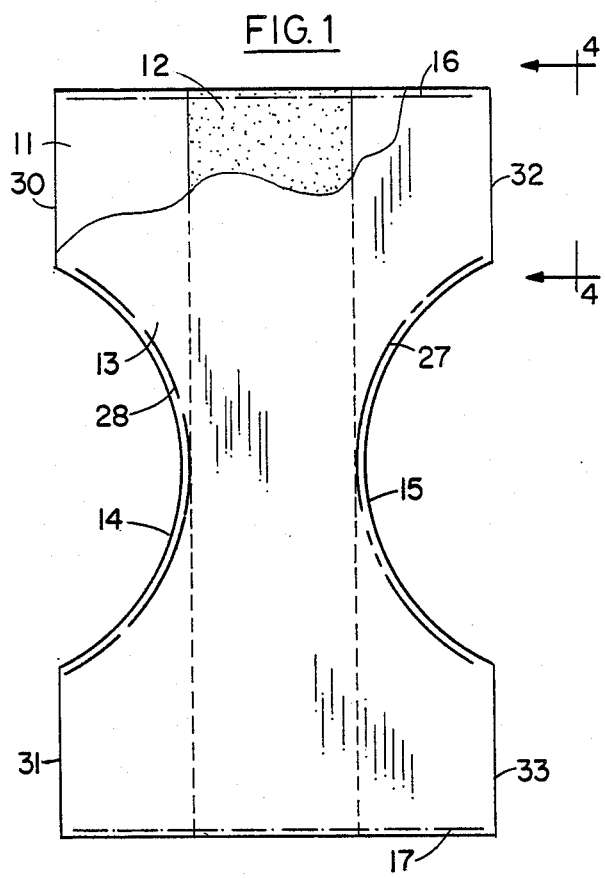
FIG. 1 is a plan of the inside-side of the blank which is made up to form the diaper.
Figure 2:
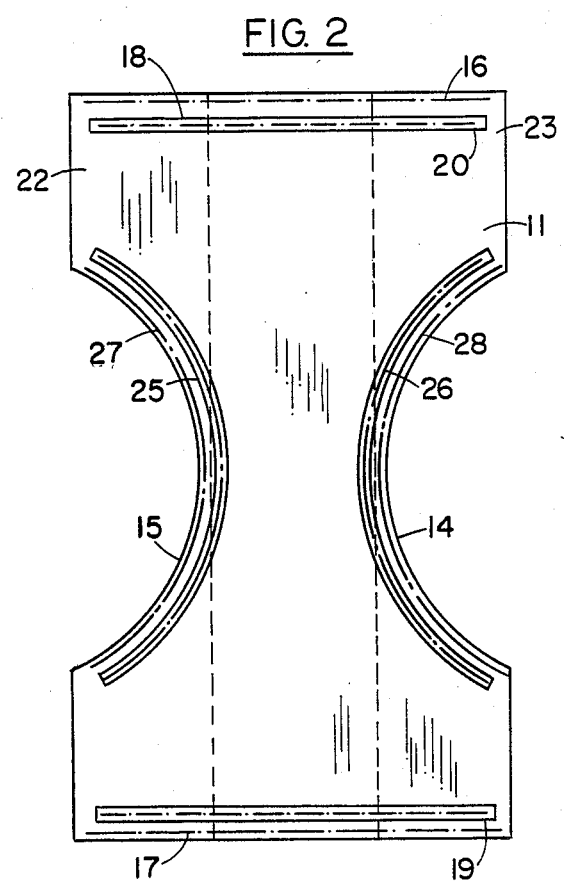
FIG. 2 is a plan of the outside-side of the same blank.
Figure 3:
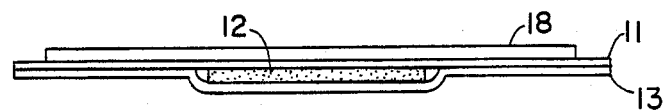
FIG. 3 is a view of the top edge of the blank of FIG. 1.
Figure 4:
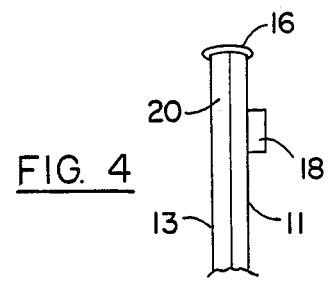
FIG. 4 is a section on the line 4—4 of FIG. 1.

When the assembly of FIGS. 1 and 2 is made it may be considered advisable to retain them against movement by applying stitchings 16 and 17 at the narrow edges; this stitching and other stitching of the finished training pants is represented by the dot and dash construction lines. Preferably, this stitching at 16 and 17 would be an edging stitch that binds in the edge to give a smooth, finished appearance, as is shown in FIG. 5.

To draw the waist of the training pants around the waist of the child to hold them up, an elastic band 18 is stitched by the stitches 20 close to the edge stitching 16. In the drawing this is shown in an extended form but it will be understood that in the pants as used the edge is gathered and expansible. A similar elastic band 19 is stitched along the edge stitching 17 just inside of it. The stitches that hold the elastic bands 18 and 19 in place could be relied on to bind the narrow ends of the sheets 11 and 13 together so as to eliminate the edge stitchings 16 and 17.

It is important to note that the elastic bands 18 and 19 do not extend to the side edges of the sheets 11 and 13. Thus, the spaces at 22 and 23 in FIG. 2 are exposed so that when the blank is sewen together to form the pants of FIG. 5 this latter stitching will not include the elastic band 18. Similar spaces are left at the ends of the elastic band 19.

To draw the leg openings somewhat tightly around the child's legs, the elastic bands 25 and 26 are sewed to the blank in the same manner that the elastics 18 and 19 are attached. Here again, the ends of these elastic strips terminate short of the long edges of the sheets so as to leave spaces like 22 and 23 for the closing stitches which will be described. Also, stitches 27 and 28 may be applied at this time to bind the edges around the leg openings and these stitches would be similar to the stitches 16 and 17.

The blank of FIGS. 1 to 4 is now folded upon itself to the form shown in FIG. 5, with the plastic, water resistant sheet 11 on the outside. The matching edges 30 and 31 are brought together and turned inwardly of the garment as is evident from FIG. 6. In like manner the matching edges 32 and 33 are brought together, turned inwardly of the garment and stitched together as is evident from FIG. 6. The stitches for 30-31 are shown at 34 and the stitches for 32-33 are shown at 35.

This inward turning of the edges 30-31 at one side and at 32-33 at the other side means that the outside of the garment has a very attractive appearance. That is, the side seams above the leg opening are barely noticeable from the outside because the edges are turned inwardly, Moreover, because the thickness of the two sheets 11 and 13 at these edges is quite small (the relative thickness is exagerated in the drawings for illustration purposes) the in turned edges at 30-31 and at 32-33 are barely noticeable and will not irritate the child.

Figure 6:
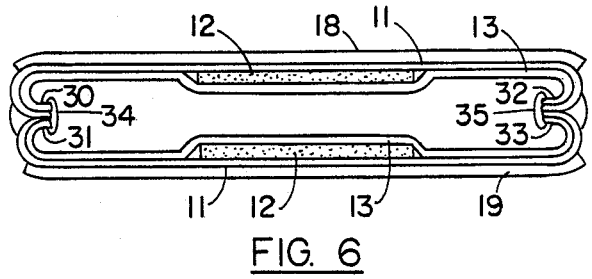
FIG. 6 is a view of the top edge of FIG. 5 on an enlarged scale and FIG. 7 is similar to FIG. 6 after the sides have been torn apart to open up the training pants.

As is apparent from FIGS. 5 and 6, the training pants can quickly and easily be drawn onto the child by lacing its legs in the leg holes and pulling upwardly. In like manner the garment can as easily be pulled off of the child by merely pulling it down and off of the legs. There are no catches or tie ribbons to be handled and the garment can be used over and over if it is not soiled.

Figure 7:
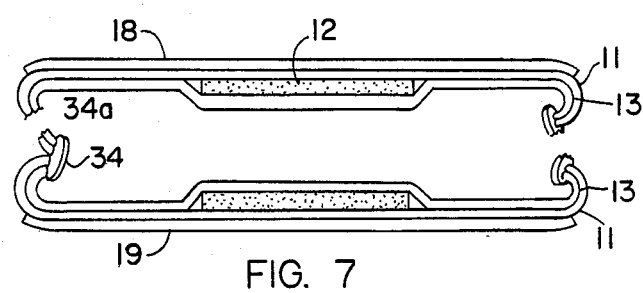

If the garment becomes soiled with excrement the garment is easily torn open at the side seams and this is the foremost feature of the invention. The stitches 34 and 35 can be broken as shown at 35a in FIG. 7, along the entire seam at 32-33 as it is pulled open and the thin threads are easily ruptured. Or, because of this fragile nature of the sheets the tear will occur as at 34a in FIG. 7. This ripping of both side seams opens the garment up to the blank form of FIGS. 1 and 2 and makes it simple to remove the soiled garment from the child.

The present invention, therefore, possesses the same feature of my above mentioned earlier patent application, namely the ease with which the side seams can be ripped open, but the present garment has an improved appearance and the entire inner lining (sheet 13) can touch the child and be comfortable. The present structure does not require the heat sealing of my prior garment.

It is not necessary to follow the order of assembly of the separate parts which is outlined above. Other sequences of putting the garment together and sewing on the elastic strips, as well as binding the edges and sewing the blank into a garment, will be obvious and may be followed.

A wide variety of products are available for practicing this invention. The waterproof sheet 11 is preferably vinyl but other thin water proof materials may be used. A suitable material is sold under the trademark "vy-cal" guage 0425 by the Vy-cal Plastics, Corp. in Conshohocken, Pa. The thin sheet 13 of absorbent material can be the non-woven interfacing identified at 101 MT 21 oz. mist cotton sold by The Stearns and Foster Co. Cincinnati, Ohio, 45215. Also, the highly absorbent strip 12 may be the cotton batting sold as product No. P 34479 by the same The Stearns & Foster Co. Similar, functional materials may be substituted for these particular ones.

It may again be stated that the other sheet is waterproof, the inner sheet covers the entire inside and is soft against the child's skin and the intermediate batting is highly water absorbent. The side seams of the garment are easily ripped apart to open it up for easy removal if they are soiled and this ripping operation is not hindered by the elastic strips or bands 18, 19, 25, 26 as they are not caught up in the stitching.

As the materials are all inexpensive and as the assembly and fabrication is easily performed the garment can be sold at a low price and the buyer does not have to worry about the fact that if it is soiled it will in most cases be thrown away. Although the invention has been described with special reference to use by children being toilet trained it is to be understood that the described features may be incorporated in a larger garment for use by adults.

I claim:

1. A toilet training pant-like garment comprising:
   a. A longitudinally elongated rectangular outer facing portion of this plastic waterproofing material, said rectangular plastic portion being about twice as long as it is wide;
   b. said rectangular outer facing portion having a circular cutout in each of its longitudinally extending margins, said cutouts being symmetrical with respect to longitudinal and transverse axes of said rectangular outer facing portion, being equidistantly removed from respective longitudinal extremities of said rectangular outer facing portion, approaching one another at the longitudinal midpoint of said rectangular outer facing portion, being spaced from one another a distance about one third the width of said rectangular outer facing portion at said longitudinal midpoint of said rectangular outer facing portion and having length along said longitudinally extending margins of said rectangular outer facing portion of about half the longitudinal length of said rectangular outer facing portion;
   c. A longitudinally elongated rectangular non-woven film inner facing portion of cellulosic fibers, said rectangular fiber portion being about twice as long as it is wide;
   d. said rectangular inner facing portion having a circular cutout in each of its longitudinally extending margins, said cutouts being symmetrical with respect to longitudinal and transverse axes of said rectangular inner facing portion, being equidistantly removed from respective longitudinal extremities of said rectangular inner facing portion, approaching one another at the longitudinal midpoint of said rectangular inner facing portion, being spaced from one another a distance about one third the width of said rectangular inner facing portion at said longitudinal midpoint of said rectangular inner facing portion and having length along said longitudinally extending margins of said rectangular inner facing portion of about half the longitudinal length of said rectangular inner facing portion, said inner facing portion being coextensive with said outer facing portion;
   e. a rectangular strip of highly moisture absorbent material extending longitudinally the length of said inner and outer rectangular portions, having longitudinal extremities in co-terminal relationship with respective longitudinal extremities of said inner and outer rectangular portions, having width substantially equal to distance between said circular cutouts of said inner rectangular portion and of said outer rectangular portion at position of closest approach of said cutouts formed in said respective longitudinally extending edges of said inner and outer rectangular portions;
   f. first and second pairs of rows of stitching securing said water-impervious sheet to said film;
      1. rows of said first pair of rows of stitching being at and extending the transverse width of said respective longitudinal extremities of said water-impervious sheet and said film edges;
      2. rows of said second pair of rows of stitching being at respective margins of said water-impervious sheet and said film defining said circular cutouts and extending the arcuate length of said cutouts;
   g. thread stitches defining said rows of stitching being substantially normal to lines defined by juncture of said water-impervious sheet and said film at said longitudinal extremities of said water-impervious sheet and said film edges margins of said water-impervious sheet and said film defining said circular cutouts;
   h. a first pair of elastic strips secured to said water-impervious sheet, each strip of said first pair being proximate and parallel with a longitudinal extremity of said water-impervious sheet portion and spaced away from said proximate longitudinal extremity a distance of at least about the width of said strip and inboard of said respective row of said first row of stitching;
   i. a second pair of elastic strips secured to said water-impervious sheet portion, each strip of said second pair being proximate to, inboard of and parallel with a portion of a longitudinally extending edge of said water-impervious sheet film defining one of said cutouts, being spaced away from said edge of said water-impervious sheet a distance of at least the width of said strip and inboard of said respective row of said second row of stitching;

j. said strips being stretched when secured to said film;
k. said water-impervious sheet, said film and said water-absorbent sheet being folded generally along the transverse axis with portions of said water-absorbent sheet on respective sides of said transverse axis facing one another so that edge portions of said water-impervious sheet on the oppositely facing surface of said water-impervious sheet from said edge portions of said film left uncovered by said rectangular sheet of water-absorbing material at said longitudinally extending margins of said film which are intermediate said arcuate cutouts and said longitudinal extremities of said film along respective longitudinally extending margins of said film, are facingly contacting and at least one pair of said facingly contacting film edge portions are destructably releasably connected one to another;
l. said elastic strips being stretched relative to said film when applied to said film so that upon application to said film, said strips contract and cause said film, when formed in said pant-like garment, to pucker about said leg openings and at said longitudinal extremities of said sheet which define a waist opening of said garment, said puckering occurring proximate to but slightly spaced away from an edge boundary of said garment to which said respective elastic strip is most proximate, said puckering causing said garment to only intermittently contact said wearer at the edge boundaries of said garment.

2. The garment of claim 1 wherein said thin plastic waterproof material is vinyl.

3. The garment of claim 2 wherein said highly absorbent material is cotton batting.

4. The garment of claim 1 wherein said highly absorbent material is cotton batting.

* * * * *